United States Patent [19]

Mori et al.

[11] Patent Number: 5,550,302
[45] Date of Patent: Aug. 27, 1996

[54] METHOD FOR PRODUCING AN ALCOHOL AND CATALYST PRECURSOR USEFUL FOR THE METHOD

[75] Inventors: Tomoyuki Mori; Kouichi Fujita; Hiroki Hinoishi, all of Okayama, Japan

[73] Assignee: Mitsubishi Chemical Corporation, Tokyo, Japan

[21] Appl. No.: 405,010

[22] Filed: Mar. 16, 1995

[30] Foreign Application Priority Data

Mar. 24, 1994 [JP] Japan .................................. 6-053532
Apr. 20, 1994 [JP] Japan .................................. 6-081748

[51] Int. Cl.$^6$ ..................... C07C 29/141; C07C 31/125
[52] U.S. Cl. ............................................ 568/881; 502/307
[58] Field of Search ............................................... 568/881

[56] References Cited

U.S. PATENT DOCUMENTS 2,009,948   4/1935   Schmidt et al. ........................ 568/881

FOREIGN PATENT DOCUMENTS 2118311   7/1972   France ................................... 568/881
316399    8/1929   United Kingdom .................... 568/881

*Primary Examiner*—Joseph E. Evans
*Attorney, Agent, or Firm*—Oblon, Spivak, McClelland, Maier, & Neustadt, P.C.

[57] ABSTRACT

A method for producing an alcohol, which comprises reacting an aldehyde with hydrogen in a gas phase in the presence of a hydrogenation catalyst to form a corresponding saturated alcohol, wherein a reduced product of a catalyst precursor composition comprising components represented by the following formula (I):

$$Cu(a)—Cr(b)—Zn(c)—Mn(d)—Ba(e)—X(f) \qquad (I)$$

wherein X is a transition metal of Group 8 or 4A of the Periodic Table, and a to f represent the contents of the respective components as converted to their oxides and have the following values:

a: 20 to 50 wt %
b: 0 to 50 wt %
c: 0 to 50 wt %
d: 0.1 to 5.0 wt %
e: 0.1 to 5.0 wt %
f: 0.01 to 3.0 wt % is used as the hydrogenation catalyst.

10 Claims, No Drawings

METHOD FOR PRODUCING AN ALCOHOL AND CATALYST PRECURSOR USEFUL FOR THE METHOD

BACKGROUND OF THE INVENTION

1. Field of the Invention

The present invention relates to a method for producing an alcohol and a catalyst precursor useful for the method, whereby in a gas phase hydrogenation reaction of an aldehyde, a corresponding saturated alcohol can be produced in good yield and with high selectivity, while suppressing formation of undesirable by-products.

2. Discussion of Background

Methods of hydrogenating aldehydes to produce corresponding alcohols are known. For example, German Patent No. 931827 discloses a method of reducing an unsaturated aldehyde in a two step reaction in a gas phase, wherein in the first step reaction, a copper-nickel catalyst supported on a carrier is used, and in the second step reaction, a modified copper-carrier catalyst is used.

Further, Japanese Unexamined Patent Publication No. 85936/1989 discloses a method wherein a gas phase hydrogenation reaction of an aldehyde is carried out using, as a hydrogenation catalyst, a composition having a selectivity-improving agent impregnated to a reduced copper oxide-zinc oxide mixture.

Still further, Japanese Unexamined Patent Publication No. 116526/1987 also discloses a method wherein hydrogenation of 2-ethylhexenal is carried out in a gas phase using a catalyst of a reduced copper oxide-zinc oxide mixture. In this case, however, three step hydrogenation reactors having different reaction conditions are employed to remove unsaturated alcohols such as 2-ethylhexenol, which are produced in small amounts.

However, the method disclosed in German Patent No. 931827 is known to have a difficulty that an unsaturated alcohol is produced together with the corresponding saturated alcohol and brings about a substantial difficulty in the purification by distillation of the saturated alcohol.

In the method disclosed in Japanese Unexamined Patent Publication No. 85936/1989, a very small amount of an ester is produced as a by-product in the reaction product, whereby it has been difficult to obtain a product which is fully satisfactory as a saturated alcohol. On the other hand, the method disclosed in Japanese Unexamined Patent Publication No. 116526/1987 has drawbacks that the process is so cumbersome that it can not easily be employed on an industrial scale, and the installation costs are high since the method requires a plurality of reactor units.

As an unsaturated alcohol produced as a by-product at the time of the hydrogenation reaction of an aldehyde, 2-ethylhexenol may, for example, be mentioned which is produced at the time of the hydrogenation reaction of 2-ethylhexenal. This unsaturated alcohol has a boiling point which is close to the boiling point of the saturated alcohol and can not easily be separated for purification on an industrial scale. The main application of a saturated alcohol such as 2-ethylhexanol is as a plasticizer, but if such an unsaturated alcohol is present even in a small amount in 2-ethylhexanol, the resulting di-2-ethylhexyl phthalate tends to be colored yellow, such being undesirable for use as a plasticizer. Accordingly, in a practical operation on an industrial scale, it is often attempted to conduct the hydrogenation reaction at a relatively high temperature so that the unsaturated alcohol is completely hydrogenated. In such a case, however, there has been a problem that formation of by-products such as esters tends to increase, and consequently, the productivity of the saturated alcohol tends to be low.

SUMMARY OF THE INVENTION

The present inventors have conducted extensive studies on the above problems and as a result, have found it possible to effectively suppress formation of undesirable by-products such as esters, ethers and unsaturated alcohols, even under a high temperature condition to maximize the reaction rate, by employing a comprising certain specific components, as the catalyst for the production of an alcohol. On the basis of this discovery, they have established a method for producing an alcohol in good yield and with a high selectivity without reducing the productivity of the saturated alcohol, and thus the present invention has been accomplished. Thus, the present invention provides a method for producing an alcohol, which comprises reacting an aldehyde with hydrogen in a gas phase in the presence of a hydrogenation catalyst to form a corresponding saturated alcohol, wherein a reduced product of a catalyst precursor composition comprising components represented by the following formula (I):

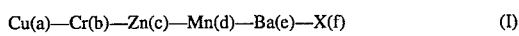

$$\text{Cu}(a)\text{—Cr}(b)\text{—Zn}(c)\text{—Mn}(d)\text{—Ba}(e)\text{—X}(f) \qquad (I)$$

wherein X is a transition metal of Group 8 or 4A of the Periodic Table, and a to f represent the contents of the respective components as converted to their oxides and have the following values:

a: 20 to 50 wt %
b: 0 to 50 wt %
c: 0 to 50 wt %
d: 0.1 to 5.0 wt %
e: 0.1 to 5.0 wt %
f: 0.01 to 3.0 wt % is used as the hydrogenation catalyst.

Further, the present invention provides a catalyst precursor composition for the production of an alcohol, which comprises components represented by the following formula (I):

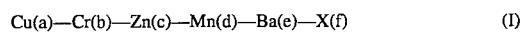

$$\text{Cu}(a)\text{—Cr}(b)\text{—Zn}(c)\text{—Mn}(d)\text{—Ba}(e)\text{—X}(f) \qquad (I)$$

wherein X is a transition metal of Group 8 or 4A of the Periodic Table, and a to f represent the contents of the respective components as converted to their oxides and have the following values:

a: 20 to 50 wt %
b: 0 to 50 wt %
c: 0 to 50 wt %
d: 0.1 to 5.0 wt %
e: 0.1 to 5.0 wt %
f: 0.01 to 3.0 wt %.

DETAILED DESCRIPTION OF THE PREFERRED EMBODIMENTS

Now, the present invention will be described in detail.

As the catalyst to be used in the method for producing an alcohol of the present invention, a reduced product of a catalyst precursor composition comprising components represented by the following formula (I):

$$Cu(a)—Cr(b)—Zn(c)—Mn(d)—Ba(e)—X(f) \quad (I)$$

is used. In the above formula (I), X is a transition metal of Group 8 or 4A of the Periodic Table, preferably Pd or Ni, or Zr or Ti, and a to f represent the contents of the respective components as converted to their oxides and may be selected in an optional combination of values within the following ranges:

a: 20 to 50 wt %
b: 0 to 50 wt %
c: 0 to 50 wt %
d: 0.1 to 5.0 wt %
e: 0.1 to 5.0 wt %
f: 0.01 to 3.0 wt %.

In the above formula, the contents of the respective components are calculated on the assumption that the respective components in the composition are converted to their oxides. Here, Cu is converted to CuO, Cr to $Cr_2O_3$, Zn to ZnO, Mn to $Mn_2O_3$, and Ba to BaO. Further, component X is converted to its stable oxide. For example, Pd is converted to PdO, Ni to NiO, Zr to $ZrO_2$, and Ti to $TiO_2$.

Specifically, in the above formula (I), it is particularly preferred to employ a catalyst precursor composition represented by the following formula (II):

$$CuO(a)—Cr_2O_3(b)—ZnO(c)—Mn_2O_3(d)—BaO(e)—X'(f) \quad (II)$$

wherein X' is a compound of a transition metal of Group 8 or 4A of the Periodic Table, and a to f represent the contents of the respective components (provided that the content of component X' is calculated as converted to its oxide) and have the following values:

a: 20 to 50 wt %
b: 0 to 50 wt %
c: 0 to 50 wt %
d: 0.1 to 5.0 wt %
e: 0.1 to 5.0 wt %
f: 0.01 to 3.0 wt %.

The conversion of component X' to its oxide, is conducted in the same manner as the above-mentioned conversion with respect to component X.

Further, in the above formula (I), it is preferred that at least one of b and c is from 0.1 to 50 wt %, and it is particularly preferred to employ a precursor composition of the following formula (III) or (IV):

$$Cu(a)—Cr(b)—Mn(d)—Ba(e)—X(f) \quad (III)$$

wherein X is as defined above, and a to f represent the contents of the respective components as converted to their oxides and have the following values:

a: 20 to 50 wt %
b: 20 to 50 wt %
d: 0.1 to 5.0 wt %
e: 0.1 to 5.0 wt %
f: 0.01 to 3.0 wt %.

$$Cu(a)—Zr(c)—Mn(d)—Ba(e)—X(f) \quad (IV)$$

wherein X is as defined above, and a to f represent the contents of the respective components as converted to their oxides and have the following values:

a: 20 to 50 wt %
c: 20 to 50 wt %
d: 0.1 to 5.0 wt %
e: 0.1 to 5.0 wt %
f: 0.01 to 3.0 wt %.

The catalyst precursor composition to be used in the present invention, can be produced by any method suitable for the production of a catalyst substance, such as a coprecipitation method or an impregnation method. Specifically, it can be prepared by coprecipitating the components other than component X in the formula (I) in the form of a mixture from an aqueous solution of metal compounds such as metal salts, converting (decomposing) the mixture to the corresponding oxides to produce metal oxides, and further impregnating to the metal oxides an aqueous solution of a salt of component X, such as an aqueous solution of its nitrate, and baking (decomposing) it in air. Component X in the above catalyst precursor composition is a transition metal of Group 8 or 4A of the Periodic Table and is present in the form of a suitable compound such as an oxide. Usually, the catalyst precursor composition of the present invention takes mainly the form of oxides. However, the catalyst precursor composition of the present invention may be in any form so long as it contains the respective components represented by the formula (I) in the specified amounts.

In some cases, the catalyst precursor composition prepared by the above method may contain a small amount of a modifying agent and may be pelettized by a conventional method such as tabletting or extrusion molding.

Before it is used for the hydrogenation reaction of an aldehyde, the above catalyst precursor composition is reduced by being heated for a few hours in the presence of a reducing agent such as hydrogen while controlling the temperature within a range of from 150° to 350° C., preferably from 170° to 300° C. It is not desirable to apply an excessively high temperature of about 350° C. or higher during the reduction, since the catalytic activities tend to be low.

As the reducing agent, it is preferred to use a dilute hydrogen stream containing from 1 to 10% of hydrogen in a diluting gas, and as the diluting gas, nitrogen gas may preferably be employed.

As the starting material aldehyde, a $C_{3-22}$ linear or branched saturated or unsaturated aldehyde may usually be used. Such aldehydes may be used alone or in combination as a mixture of aldehydes. The starting material aldehyde may contain a small amount of impurities.

Specifically, it may, for example, be propionaldehyde, isobutyraldehyde, n-butyraldehyde, n-valeraldehyde, isovaleraldehyde, 2-methylvaleraldehyde, 2-ethylhexanal, 2-ethylbutyraldehyde, methyl n-propylacetaldehyde, capronaldehyde, isocapronaldehyde, caprylaldehyde, n-nonylaldehyde, isononylaldehyde, 2-propylheptenal, 2-propyl-4-methylhexenal, n-decanal, dodecanal, tridecanal, myristicaldehyde, pentadecanal, parmitinaldehyde, stearinaldehyde, acrolein, methacrolein, ethacrolein, 2-ethyl-3-propylacrolein, or croton aldehyde.

As the starting material aldehyde, it is also possible to employ a part or whole of a mixture formed by an oxoprocess (hydroformulation) wherein an olefin is reacted with carbon monoxide and hydrogen in the presence of a catalyst to add a formyl group to one of carbon atoms of an olefinic group. As the starting material aldehyde obtained from the oxoprocess, there may, for example, be mentioned a mixture of isobutylaldehyde and n-butylaldehyde, or isononylaldehyde.

Further, the starting material aldehyde can also be obtained by a process different from the oxoprocess, such as an oxidation reaction of an olefin or a saturated hydrocarbon or an aldol condensation of a carbonyl compound. As the starting material aldehyde obtained from the aldol condensation, a mixture of 2-ethylhexenal, 2-propylheptenal and 2-propyl-4-methylhexenal, may, for example, be mentioned.

In the present invention, the aldehyde is reacted with hydrogen in a gas phase in the presence of a hydrogenation catalyst. As the hydrogen, substantially pure hydrogen gas may be used alone, but it may be supplied as an admixture with another gas inert to the aldehyde and the catalyst. As the inert gas suitable to be admixed with hydrogen, nitrogen or methane may, for example, be mentioned.

The concentration of hydrogen in the reaction zone is not critical, but hydrogen should usually be present in an excess amount exceeding the stoichiometrical amount, relative to the aldehyde to be reduced. Usually, the molar ratio of the hydrogen to the aldehyde is from about 3 to 400, preferably from 5 to 200. In the case of an aldehyde having from 2 to 12 carbon atoms, the molar ratio of the hydrogen to the aldehyde is preferably within a range of from about 3 to 30.

The temperature for the hydrogenation reaction is usually from 100° to 250° C. The temperature is preferably within a range of from 150° to 200° C. to most effectively utilize the selectivity of the hydrogenation catalyst of the present invention. The reaction pressure is usually within a range of from 0 to 10 kg/cm$^2$G. If the pressure exceeds 10 kg/cm$^2$G, such is not advantageous since a large quantity of energy is required to completely vaporize the aldehyde, although there is no problem with respect to the reaction selectivity.

In the present invention, the hydrogenation reaction can be accomplished by putting the vapor stream of the evaporated aldehyde and the hydrogen-containing gas together and bringing the combined gas in contact with the reduced product of the catalyst precursor composition of the formula (I) at the predetermined temperature and pressure. For example, the reaction is preferably conducted in a flow (continuous) system of e.g. a fixed catalyst bed reaction apparatus.

Further, the hydrogenation reaction can be carried out by isothermal reaction system or adiabatic reaction system. Especially, in the present invention, it is possible to utilize the heat of reaction as a useful heat source, for example, for generating high pressure steam, which is recycled for use in the hydrogenation reaction.

Unreacted hydrogen and aldehyde recovered from the hydrogenation reaction product can be used by recycling them to the hydrogenation reaction zone. Further, the crude alcohol product obtained, may further be purified by e.g. fractional distillation. However, the product is usually useful as a commercial product by itself without requiring a purification operation.

Now, the present invention will be described in further detail with reference to Examples. However, it should be understood that the present invention is by no means restricted by such specific Examples.

In Examples 1 to 4 and Comparative Examples 1 to 3, the catalyst precursor compositions having the following compositions, prepared by a conventional coprecipitation method, were used. The contents of the respective components are shown by wt %.

EXAMPLE 1 (Catalyst A)

To an aqueous solution of cupric nitrate trihydrate [Cu(NO$_3$)$_2$.3H$_2$O], an aqueous manganese nitrate solution was added to obtain a solution containing copper and manganese. On the other hand, ammonium dichromate [(NH$_4$)$_2$Cr$_2$O$_7$] was dissolved in aqueous ammonia to obtain a chromium-containing solution.

The above solution containing copper and manganese was heated to 60° C., and while stirring it at the same temperature, the above chromium-containing solution was dropwise added thereto. At that time, a precipitate partly formed. But, dilute nitric acid was further added to adjust the pH, and stirring was continued to complete formation of the precipitate. Then, the precipitate was collected by filtration, and the obtained precipitate was thoroughly washed with water. The precipitate thus obtained was dried at 100° C. for 12 hours to obtain a powder comprising copper, chromium and manganese. To this powder, a warm solution of barium hydroxide [Ba(OH)$_2$.8H$_2$O] was added, and the mixture was evaporated to dryness with stirring.

To the powder comprising copper, chromium, manganese and barium thus obtained, an aqueous nickel nitrate solution was added, and the mixture was stirred and mixed at 100° C. and evaporated to dryness. The obtained powder comprising copper-chromium-manganese-barium-nickel was calcined in air at a temperature of 350° C. for three hours to obtain the following catalyst A.

CuO(39.4)—Cr$_2$O$_3$(41.9)—Mn$_2$O$_3$(1.5)—BaO (1.7)—NiO(1.0)

(This catalyst A may be represented by the formula (I) as follows:  Cu(31.5)—Cr(28.7)—Mn(1.0)—Ba(1.5)—Ni(0.8).)

EXAMPLE 2 (Catalyst B)

In the same manner as in Example 1, the following catalyst B was prepared.

CuO(39.4)—Cr$_2$O$_3$(41.9)—Mn$_2$O$_3$(1.5)—BaO(1.7)—PdO(0.1)

(This catalyst B may be represented by the formula (I) as follows:  Cu(31.5)—Cr(28.7)—Mn(1.0)—Ba(1.5)—Pd(0.09).)

EXAMPLE 3 (Catalyst C)

In the same manner as in Example 1, the following catalyst C was prepared.

CuO(39.4)—Cr$_2$O$_3$ (41.9)—Mn$_2$O$_3$(1.5)—*BaO*(1.7)—ZrO$_2$(1.0)

(This catalyst C may be represented by the formula (I) as follows:  Cu(31.5)—Cr(28.7)—Mn(1.0)—Ba(1.5)—Zr(0.7).)

EXAMPLE 4 (Catalyst D)

In the same manner as in Example 1, the following catalyst D was prepared.

CuO(40.2)—ZnO(35.9)—Mn$_2$O$_3$(1.5)—BaO(1.7)—NiO(1.0)

(This catalyst D may be represented by the formula (I) as follows:  Cu(32.1)—Zn(28.8)—Mn(1.0)—Ba(1.5)—Ni(0.8).)

Comparative Example 1 (Catalyst E)

In the same manner as in Example 1, the following catalyst E was prepared.

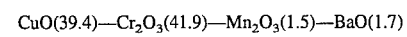
CuO(39.4)—Cr$_2$O$_3$(41.9)—Mn$_2$O$_3$(1.5)—BaO(1.7)

(This catalyst E may be represented by the formula (I) as follows: Cu(31.5)—Cr(28.7)—Mn(1.0)—Ba(1.5).)

COMPARATIVE EXAMPLE 2 (Catalyst F)

In the same manner as in Example 1, the following catalyst F was prepared.

CuO(37.8)—Cr$_2$O$_3$(36.1)—Mn$_2$O$_3$(1.8)

(This catalyst F may be represented by the formula (I) as follows: Cu(30.2)—Cr(24.7)—Mn(1.3).)

Comparative Example 3 (Catalyst G)

In the same manner as in Example 1, the following catalyst G was prepared.

CuO(49.3)—ZnO(45.1)

(This catalyst G may be represented by the formula (I) as follows: Cu(39.4)—Zn(36.2).)

EXAMPLES 5 TO 8 AND COMPARATIVE EXAMPLES 4 TO 6

Into a stainless steel single tube reactor having an inner diameter of about 2.4 cm (1 inch), 10 cc of each catalyst was charged, then a nitrogen gas was supplied to the reactor, and the internal temperature of the reactor was raised to 170° C. Then, the nitrogen gas was switched to nitrogen gas containing 10 vol % of hydrogen, and the internal temperature of the reactor was raised to 250° C. at a rate of 2° to 3° C./min. Then, with respect to each catalyst, reduction was carried out for about 3 hours. Further, the internal temper of the reactor was raised to 300° C. at a rate of 2° to 3° C./min, and then reduction by the above catalyst was conducted for about two hours.

After completion of the reduction, the internal temperature of the reactor was set at 180° C., and the above nitrogen gas was switched to nitrogen gas containing at least 90 vol % of hydrogen, and the pressure in the reactor was maintained at 4.6 kg/cm$^2$G. Then, 2- ethylhexenal (hereinafter referred to as EPA) having a purity of at least 99% obtained by a hydroformulation reaction of propylene by a rhodium-containing catalyst and an aldol condensation by a sodium hydroxide catalyst, was completely vaporized and supplied together with the above-mentioned hydrogen-containing gas to the above reactor.

The supply rate of EPA was 15 cc/hr as a liquid base, and the supply rate of the hydrogen-containing gas was controlled so that the molar ratio of hydrogen/EPA would be about 22. The obtained reaction product was collected by a condenser and analyzed by gas chromatography. The results are shown in Table 1.

TABLE 1

|  | Examples | | | | Comparative Examples | | |
|---|---|---|---|---|---|---|---|
|  | 5 | 6 | 7 | 8 | 4 | 5 | 6 |
| Hydrogenation catalyst | A | B | C | D | E | F | G |
| Conversion of EPA[1] (%) | 100 | 100 | 100 | 100 | 99.8 | 99.4 | 99.8 |
| Yield EH[2] (%) | 99.6 | 99.6 | 99.6 | 99.6 | 99.1 | 97.2 | 99.0 |

TABLE 1-continued

|  | Examples | | | | Comparative Examples | | |
|---|---|---|---|---|---|---|---|
|  | 5 | 6 | 7 | 8 | 4 | 5 | 6 |
| u-2EH[3] (%) | — | — | — | — | 0.3 | 0.4 | 0.2 |
| 2HA[4] (%) | 0.1 | 0.1 | 0.1 | 0.1 | 0.2 | 1.4 | 0.2 |
| High boiling point substances | 0.3 | 0.3 | 0.3 | 0.3 | 0.2 | 0.4 | 0.4 |

[1] EPA: 2-ethylhexenal
[2] 2EH: 2-ethylhexanol
[3] u-2EH: 2-ethylhexenol
[4] 2HA: 2-ethylhexanal As is evident from the results in Table 1, in the hydrogenation reaction according to the method of the present invention, formation of by-products, particularly unsaturated alcohols, can effectively be suppressed. Accordingly, when the obtained alcohols are used as plasticizers, the coloring test performance is remarkably improved.

By conducting a vapor phase hydrogenation reaction of aldehydes using the reduced product of the specific catalyst precursor composition of the present invention, it is possible to suppress formation of by-products such as esters, ethers and unsaturated alcohols even under a high temperature condition and to produce corresponding saturated alcohols in good yield and with high selectivity. Further, according to the present invention, the heat of reaction generated during the hydrogenation can be effectively utilized as a heat source, which is variable from the viewpoint of industrial application.

What is claimed is:

1. A method for producing an alcohol, which comprises reacting an aldehyde with hydrogen in a gas phase in the presence of a hydrogenation catalyst to form a corresponding saturated alcohol, wherein a reduced product of a catalyst precursor composition comprising components represented by the following formula (I):

Cu(a)—Cr(b)—Zn(c)—Mn(d)—Ba(e)—X(f)   (I)

wherein X is a transition metal of Group 8 or 4A of the Periodic Table, and a to f represent the contents of the respective components as converted to their oxides and have the following values:

a: 20 to 50 wt %
b: 0 to 50 wt %
c: 0 to 50 wt %
d: 0.1 to 5.0 wt %
e: 0.1 to 5.0 wt %
f: 0.01 to 3.0 wt % is used as the hydrogenation catalyst.

2. The method for producing an alcohol according to claim 1, which comprises reacting an aldehyde with hydrogen in a gas phase in the presence of a hydrogenation catalyst to form a corresponding saturated alcohol, wherein a reduced product of a catalyst precursor composition represented by the following formula (II):

CuO(a)—Cr$_2$O$_3$(b)—ZnO(c)—Mn$_2$O$_3$ (d)—BaO(e)—X'(f)   (II)

wherein X' is a compound of a transition metal of Group 8 or 4A of the Periodic Table, and a to f represent the contents of the respective components (provided that the content of component X' is calculated as converted to its oxide) and have the following values:

a: 20 to 50 wt %
b: 0 to 50 wt %
c: 0 to 50 wt %
d: 0.1 to 5.0 wt %
e: 0.1 to 5.0 wt %
f: 0.01 to 3.0 wt % is used as the hydrogenation catalyst.

3. The method for producing an alcohol according to claim 1, wherein in the formula (I), at least one of b and c is from 0.1 to 50 wt %.

4. The method for producing an alcohol according to claim 1, wherein the hydrogenation catalyst is a reduced product of a catalyst precursor composition comprising components represented by the following formula (III):

$$Cu(a)-Cr(b)-Mn(d)-Ba(e)-X(f) \qquad (III)$$

wherein X is as defined in claim 1, and a to f represent the contents of the respective components as converted to their oxides and have the following values:

a: 20 to 50 wt %
b: 20 to 50 wt %
d: 0.1 to 5.0 wt %
e: 0.1 to 5.0 wt %
f: 0.01 to 3.0 wt %.

5. The method for producing an alcohol according to claim 1, wherein the hydrogenation catalyst is a reduced product of a catalyst precursor composition comprising components represented by the following formula (IV):

$$Cu(a)-Zn(c)-Mn(d)-Ba(e)-X(f) \qquad (IV)$$

wherein X is as defined in claim 1, and a to f represent the contents of the respective components as converted to their oxides and have the following values:

a: 20 to 50 wt %
c: 20 to 50 wt %
d: 0.1 to 5.0 wt %
e: 0.1 to 5.0 wt %
f: 0.01 to 3.0 wt %.

6. The method for producing an alcohol according to claim 1, wherein component X is Pd or Ni.

7. The method for producing an alcohol according to claim 1, wherein component X is Zr or Ti.

8. The method for producing an alcohol according to claim 1, wherein the hydrogenation catalyst is a reduced product obtained by heating the catalyst precursor composition of the formula (I) in the presence of hydrogen within a temperature range of from 150° to 350° C.

9. The method for producing an alcohol according to claim 1, wherein the reaction is carried out at a temperature of from 100° to 250° C. under a pressure of from 0 to 10 kg/cm²G.

10. The method for producing an alcohol according to claim 1, wherein the aldehyde is 2-ethylhexenal.

* * * * *